US010398625B2

(12) United States Patent
Sandford et al.

(10) Patent No.: US 10,398,625 B2
(45) Date of Patent: Sep. 3, 2019

(54) MEDICAL CONTAINERS WITH TEREPHTHALATE PLASTICIZER FOR STORING RED BLOOD CELL PRODUCTS

(71) Applicant: Fenwal, Inc., Lake Zurich, IL (US)

(72) Inventors: Craig Sandford, Buffalo Grove, IL (US); Yoshikazu Mizobuchi, Mundelein, IL (US); Daniel Lynn, Spring Grove, IL (US)

(73) Assignee: FENWAL, INC., Lake Zurich, IL (US)

( * ) Notice: Subject to any disclaimer, the term of this patent is extended or adjusted under 35 U.S.C. 154(b) by 164 days.

(21) Appl. No.: 13/800,682

(22) Filed: Mar. 13, 2013

(65) Prior Publication Data

US 2014/0276527 A1 Sep. 18, 2014

(51) Int. Cl.
*A61M 5/32* (2006.01)
*A61J 1/10* (2006.01)
*A01N 1/02* (2006.01)
*A61J 1/14* (2006.01)

(52) U.S. Cl.
CPC .............. *A61J 1/10* (2013.01); *A01N 1/0263* (2013.01); *A61J 1/1468* (2015.05)

(58) Field of Classification Search
CPC ......... A61J 1/10; A61J 1/00; A61J 2001/1468
USPC ........................................................ 604/408
See application file for complete search history.

(56) References Cited

U.S. PATENT DOCUMENTS

| 3,384,607 | A | 5/1968 | Magne et al. |
| 4,286,597 | A | 9/1981 | Gajewski |
| 4,300,559 | A | 11/1981 | Gajewski |
| 4,301,800 | A | 11/1981 | Collins |
| 4,326,025 | A | 4/1982 | Buckles |
| 4,346,710 | A * | 8/1982 | Thanawalla et al. ......... 604/408 |
| 4,375,509 | A | 3/1983 | Buckles |
| 4,451,259 | A | 5/1984 | Geissler |
| 4,507,123 | A | 3/1985 | Yoshida |
| 4,507,387 | A | 3/1985 | Gajewski |
| 4,657,541 | A | 4/1987 | Ichikawa et al. |
| 4,710,532 | A * | 12/1987 | Hull ................. C08K 5/11 524/310 |
| 4,943,287 | A | 7/1990 | Carmen |
| 5,026,347 | A | 6/1991 | Patel |
| 5,079,002 | A | 1/1992 | Nagai |
| 5,100,401 | A | 3/1992 | Patel |

(Continued)

FOREIGN PATENT DOCUMENTS

| CN | 101215398 A | 7/2000 |
| CN | 1273129 A | 11/2000 |

(Continued)

OTHER PUBLICATIONS

H.R. Hill et al., The Effects of Polyvinyl Chloride and Polyolefin Blood Bags on Red Blood Cells Stored in a New Additive Solution, Vox Sanguinis, vol. 81, No. 3, Oct. 1, 2001, pp. 161-166. XP55045602, ISSN: 0042-9007.

(Continued)

*Primary Examiner* — Andrew J Mensh
(74) *Attorney, Agent, or Firm* — Cook Alex Ltd.

(57) ABSTRACT

Containers for the storage of red blood cell compositions are disclosed. The container walls are made of a plastic composition that includes a polymeric material and at least one extractable agent that includes a terephthalate ester in an amount effective to suppress hemolysis in red blood cells.

23 Claims, 1 Drawing Sheet

(56) References Cited

U.S. PATENT DOCUMENTS

| | | |
|---|---|---|
| 5,236,716 A | 8/1993 | Carmen |
| 5,248,531 A | 9/1993 | Nagai |
| 5,252,373 A | 10/1993 | Ganske et al. |
| 5,382,526 A | 1/1995 | Gajewski |
| 5,637,819 A | 6/1997 | Rogers |
| 5,713,694 A | 2/1998 | Monda |
| 5,769,839 A | 6/1998 | Carmen |
| 6,468,258 B1 | 10/2002 | Shang |
| 6,545,096 B1 * | 4/2003 | Honda ............ C08J 9/18 525/240 |
| 6,675,560 B2 | 1/2004 | Gott |
| 7,276,621 B2 | 10/2007 | Cook |
| 7,595,421 B2 | 9/2009 | Grass |
| 7,629,413 B2 | 12/2009 | Godwin |
| 7,754,198 B2 | 7/2010 | Whitehead |
| 7,964,658 B2 | 6/2011 | Grass |
| 8,026,314 B2 | 9/2011 | Hansel |
| 8,329,796 B2 | 12/2012 | Grass |
| 8,372,912 B2 | 2/2013 | Olsen |
| 8,669,311 B2 | 3/2014 | Colle |
| 9,828,488 B2 | 11/2017 | Sakai |
| 2003/0014948 A1 | 1/2003 | Gott et al. |
| 2003/0157150 A1 | 8/2003 | Lee |
| 2004/0078022 A1 * | 4/2004 | Donart ............ A61J 1/05 604/408 |
| 2007/0037926 A1 | 2/2007 | Olsen et al. |
| 2008/0132712 A1 | 6/2008 | Denoux et al. |
| 2008/0200595 A1 | 8/2008 | Hinault et al. |
| 2009/0149586 A1 | 6/2009 | De Quadros Junior et al. |
| 2009/0287007 A1 | 11/2009 | Abraham et al. |
| 2010/0305255 A1 | 12/2010 | Grass |
| 2011/0117647 A1 | 5/2011 | Mayaudon |
| 2011/0281987 A1 | 11/2011 | Godwin |
| 2013/0011824 A1 | 1/2013 | Chan |
| 2013/0137789 A1 | 5/2013 | Olsen |
| 2013/0303640 A1 | 11/2013 | Kim |
| 2013/0310472 A1 | 11/2013 | Becker |
| 2013/0338276 A1 | 12/2013 | Becker |
| 2014/0162045 A1 | 6/2014 | Bourassa |
| 2014/0336319 A1 | 11/2014 | Kim |

FOREIGN PATENT DOCUMENTS

| | | |
|---|---|---|
| CN | 101798428 A | 8/2010 |
| CN | 101979434 A | 2/2011 |
| CN | 102503975 A | 6/2012 |
| CN | 102634127 A | 8/2012 |
| CN | 103642150 A | 3/2014 |
| DE | 3200 264 | 7/1983 |
| DE | 3444155 A1 | 6/1985 |
| DE | 202010004386 U1 | 6/2010 |
| DE | 10 2010 003415 | 10/2011 |
| DE | 102010003415 A1 | 10/2011 |
| DE | 202013105795 U1 | 2/2014 |
| EP | 0138 147 | 4/1985 |
| EP | 1864 964 | 12/2007 |
| EP | 2114 854 | 11/2009 |
| EP | 2810 982 | 12/2014 |
| GB | 1172743 A | 12/1969 |
| GB | 1279939 A | 6/1972 |
| JP | S58162649 A | 9/1983 |
| JP | S5933343 A | 2/1984 |
| JP | S6023621 A | 2/1985 |
| JP | H067450 A | 1/1994 |
| JP | H0824329 A | 1/1996 |
| JP | H0827341 A | 1/1996 |
| JP | H09194818 A | 7/1997 |
| JP | H1149909 A | 2/1999 |
| JP | 2003 171288 | 6/2003 |
| JP | 2003165881 A | 6/2003 |
| JP | 2003226788 A | 8/2003 |
| JP | 2003253072 A | 9/2003 |
| JP | 2008074955 A | 4/2008 |
| JP | 2014223182 A | 12/2014 |
| JP | 2015089931 A | 5/2015 |
| JP | 5933343 B2 | 6/2016 |
| WO | WO 2009/118261 | 10/2009 |
| WO | WO 2011/023590 A1 | 3/2011 |
| WO | WO 2012/169081 A1 | 12/2012 |
| WO | WO 2013/043658 | 3/2013 |
| WO | WO 2013/043711 | 3/2013 |
| WO | WO 2013/084707 A1 | 6/2013 |
| WO | WO 2013/100875 | 7/2013 |
| WO | WO 2014/031852 | 2/2014 |
| WO | WO 2014/076717 | 5/2014 |
| WO | WO 2014/135055 | 9/2014 |
| WO | WO 2014/185872 | 11/2014 |

OTHER PUBLICATIONS

C.J. Draper et al., Biochemical and Structural Changes in RBCs Stored With Different Plasticizers: The Role of Hexanol, Transfusion, vol. 42, No. 7, Jul. 1, 2002, pp. 830-835, XP55045604, ISSN: 0041-1132.

Database WPI, Week 200403, Thomson Scientific, London, GB; AN 2004-026123, XP002688187.

Chembumukulam, S. B., et al., PVC Containers for Collection and Storage of Blood and Blood Components, WPI/Thomson, vol. 2008, No. 17, Dec. 28, 2007, XP002617312.

Chembumukulam, S. B., et al., PVC Containers for Collection and Storage of Blood and Blood Products, Indian Patent App. IN2006CH00254, (254/CHE/2006), Dec. 28, 2007, pp. 1-22, XP55046025.

European Extended Seach Report dated Jul. 18, 2014 for EP Application No. 13194083.5-1660.

Yuji, Haishima, et al., Screening Study on Hemolysis Suppression . . . Chloride, Journal of Biomedical Materials Research Part B: Applied Biomaterials, vol. 102, No. 4, Oct. 24, 2013, pp. 721-728, XP055127428, ISSN: 1552-4973, DOI: 10.1002/jbm.b. 33052.

Simmchen, Juliane, et al., Progress in the Removal of . . . Plasticizer in Blood Bags, vol. 26, No. 1, dated Jan. 1, 2012, pp. 27-37, XP028338542, ISSN: 0887-7963, DOI: 10.1016/J.TMRV.2011.06. 001.

Dumont, Larry J., et al., Exploratory in Vitro Study of Red Blood Cell Storage . . . Plasticizer, Transfusion, vol. 52, No. 7, dated Dec. 30, 2011, pp. 1439-1445, XP055127658 ISSN : 0041-1132, DOI 10.1111/j.1537-2995.2011.03506.x.

Benaniba et al., "Stabilization of PVC by Epoxidized Sunflower Oil in the Presence of Zinc and Calcium Stearates", Polymer Degradation and Stability, 2003, pp. 245-249, vol. 82, No. 2.

Bui et al., "Human Exposure, Hazard and Risk of Alternative Plasticizers to Phthalate Esters", Science of the Total Environment; Jan. 2016, pp. 451-467, vol. 541.

Opinion on the Safety of Medical Devices Containing DEHP-Plasticized PVC or Other Plasticizers on Neonates and Other Groups Possibly at Risk by SCENIHR dated Feb. 6, 2008.

* cited by examiner

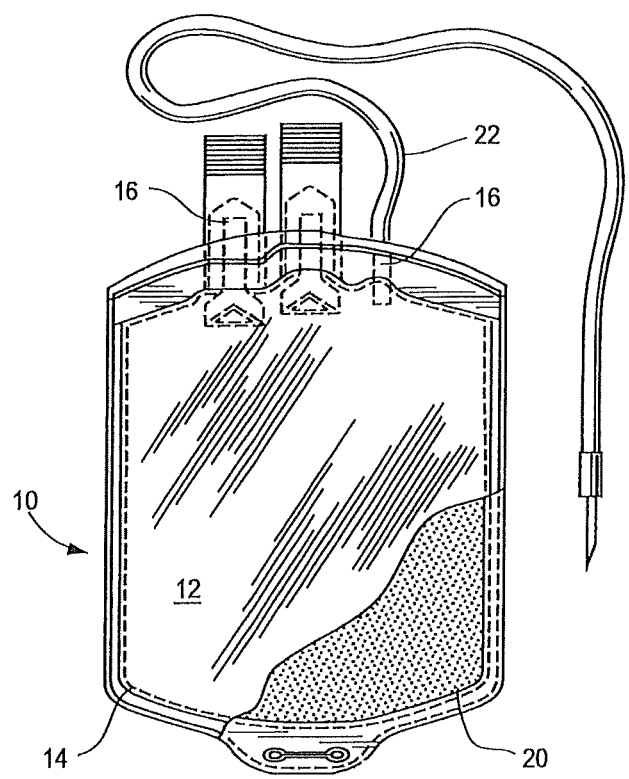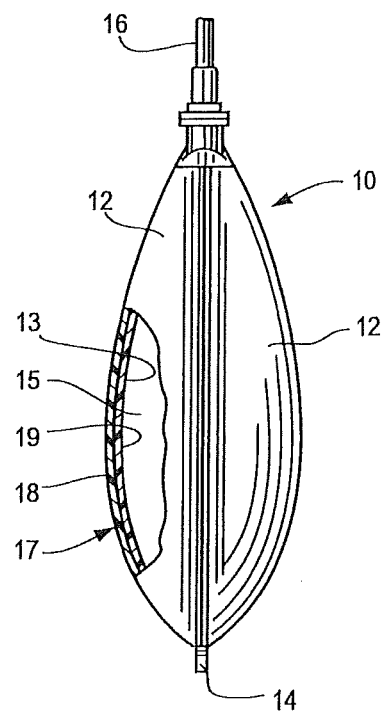

MEDICAL CONTAINERS WITH TEREPHTHALATE PLASTICIZER FOR STORING RED BLOOD CELL PRODUCTS

BACKGROUND

Red blood cells are often separated from whole blood and collected for later transfusion to a patient in need of red blood cells. For example, red blood cells (hereinafter "RBCs") may be administered to a patient suffering from a loss of blood due to trauma, as a post-chemotherapy treatment, or as part of a treatment of one or more blood borne diseases, such as certain anemias and the like. Unless administered immediately after collection from a donor, RBCs must typically be stored for some period of time prior to transfusion. The storage period may be anywhere from a few days to several weeks.

Prolonged storage of RBCs can (negatively) affect RBC function. In order for the RBCs to be suitable for transfusion to the recipient, RBCs must maintain adequate cell function and metabolism. For example, RBCs must maintain an adequate concentration of adenosine triphosphate (ATP) and 2,3-DPG. In addition, the presence of lactate must not be too high in the stored RBCs. Still further, stored RBCs must have acceptably low levels of hemolysis. Typically, an acceptable level of hemolysis is below 1.0% (in, for example, the U.S.) and 0.8% (in Europe) after 42 day storage.

During storage, concentrated RBCs and the additive solutions in which they are stored are typically kept in a sealed container, usually made of a plastic material. Most typically, the containers approved for the collection of whole blood and the storage of RBCs are made of a polyvinyl chloride (PVC). Inasmuch as polyvinyl chloride can be somewhat rigid or brittle, a plasticizer is typically incorporated into the PVC. One example of a currently known and used plasticizer for medical grade PVC is di-ethylhexyl phthalate ester or DEHP. Other plasticizers that have been used with PVC or other polyolefin materials include TEHTM, and the family of citrate esters described in U.S. Pat. No. 5,026,347, the contents of which is also incorporated by reference herein. In addition, epoxidized oil is often added as a secondary plasticizer to one or more of the plasticizers described above.

As reported in U.S. Pat. No. 5,026,347 and other literature, such as Rock, et al. "Incorporation of plasticizer into red cells during storage," *Transfusion*, 1984; Horowitz et al. "Stablization of RBCs by the Plasticizer, Di(ethylhexyl) phthalate," *Vox Sarguinis*, 1985, certain plasticizers may have a beneficial effect on the storage life of RBCs. More particularly, plasticizers such as DEHP and the family of citrate esters have been found to suppress hemolysis of RBCs stored in containers that include such leachable plasticizers. International Patent Application No. PCT/US2012/056100, filed Sep. 19, 2012 and incorporated by reference herein in its entirety, discloses plastic containers plasticized with 1,2-cyclohexanedicarboxylic acid diisononyl ester (or DINCH) for the storage of red blood cells with acceptable hemolysis levels.

While DEHP plasticized containers have worked well for the storage of red cells, the use of other container materials that assist in providing a suitable storage environment for red blood cells remains a topic of keen interest. Thus, it would be desirable to provide a container for RBCs wherein the container is at least substantially free of any leachable phthalate plasticizer but an extractable agent such as a plasticizer that is effective in suppressing hemolysis in red blood cells. Also, as used herein, the term "extractable agent" includes extractable plasticizers but also may include agents that act as plasticizers for some materials (e.g., PVC), but do not necessarily act as plasticizers relative to other materials.

SUMMARY

In one aspect, the present disclosure is directed to a biocompatible container for storing red blood cells and red blood cell products. The container includes one or more container walls defining an interior chamber. The container wall(s) is made of a composition that includes a polymeric material and at least one extractable agent that is or includes a terephthalate ester in an amount effective to suppress hemolysis in red blood cells.

In another aspect, the present disclosure is directed to a red blood cell product that includes a container having one or more container wall(s) defining an interior chamber. The container wall is made of a composition that includes a polymeric material and at least one extractable agent that is or includes a terephthalate ester in an amount effective to suppress hemolysis in red blood cells. A suspension of red blood cells is contained within the interior chamber and includes concentrated red blood cells and an additive solution that includes a nutrient and a buffer.

BRIEF DESCRIPTION OF THE DRAWINGS

FIG. 1 is a plan view of a typical RBC storage container used for storing the RBC suspensions and/or compositions described herein; and FIG. 2 is a side view of the container of FIG. 1.

DETAILED DESCRIPTION

Disclosed herein are containers for holding red blood cells (RBC) and red blood cell products during a period of storage wherein the container is made of a plastic material including at least one extractable agent such as a plasticizer which is capable of suppressing hemolysis in the stored RBC. More particularly, the container typically is made of a plastic material such as, but not limited to, polyvinyl chloride and at least one extractable agent that is or includes a terephthalate ester. The RBC product includes concentrated RBCs that have typically been combined with an additive solution selected to maintain cell function and metabolism of the RBCs during prolonged storage (e.g., at least about 42 days and possibly even up to at least 49 and/or 56 days). The red blood cells or RBC product is intended for transfusion to a patient.

RBC products include RBC concentrate and an additive solution. Concentrated RBCs are derived from whole blood either by manual or automated separation collection techniques which will be known to those skilled in the art. RBC concentrates may include some residual amount of plasma. In one embodiment, the RBC concentrate may have most of its plasma removed as described, for example, in International Application Publication WO/2011/049709, incorporated herein by reference.

As indicated above, the RBC and RBC products described herein may be provided in a container that is suitable for the long term storage of RBCs. Preferably, containers for storing the RBC compositions disclosed herein are made of a polymeric material. The containers may be permeable to oxygen or at least semi-permeable to oxygen. As shown in FIGS. 1 and 2, container 10 may include one or more container walls 12 which define an interior chamber 15 for receiving the RBC composition 20. In one embodiment, two sheets made of a polymeric material are brought together and sealed along their peripheries 14 by, for example, heat sealing (e.g., RF) to form container 10. Other ways of making container 10 will be known to those of skill in the art and are within the scope of the present disclosure.

As shown in FIG. 2, container wall 12 includes an outer surface 17 and an inner surface 13 which contacts the RBCs stored in the container. In one embodiment, container wall 12 may be made of a multiple sheet (18, 19) laminate wherein inner surface 13 is made of one material and outer surface 17 is made of a different material. In either embodiment, container 10 may include one or more access ports 16 for connection with tubing 22, docking devices and the like to establish flow into and out from the interior chamber 15 of container 10.

In another embodiment, containers useful in the storage of RBCs as described herein include container walls that are single sheets made in whole or at least in part of a material that includes at least one or more polymeric compounds and at least one extractable agent that is or includes a terephthalate ester in an amount effective to suppress hemolysis in RBCs and still maintain the structural integrity and biocompatibility of container 12 during manufacture, sterilization and use. The polymeric material may be blended together with the terephthalate ester and formed into flat sheets that are sealed together in the manner described above.

By way of example only, and not limitation, containers of the type described herein may have a container sheet (wall) thickness of between approximately 0.010 to 0.018 inches. They may include a non-smooth or any surface finish that minimizes sheet sticking. Typically, containers of the type described herein may have a container volume (i.e., interior chamber volume) of approximately 150 ml to 4 L. The containers of the present disclosure are preferably sterilized by autoclaving and such autoclavable containers may typically have a 70-85 durometer (Shore A).

The polymeric material may be preferably made from or otherwise include polyvinyl chloride. In an alternative embodiment, the polymeric material may be one or more non-PVC polyolefin homopolymers, co-polymers or blends thereof. Examples of suitable non-PVC polyolefins include polypropylene, polyethylene, including ultra low density polyethylene (ULDPE) and very low density polyethylene (VLDPE). Other suitable compounds that may be used in the plastic materials of the containers or as part of the blend for making the plastic materials include ethylene vinylacetate (EVA) and block co-polymers such as Kraton. Exemplary formulations and/or polyolefins, polyolefin blends or other polymeric compounds which are useful, either alone or in combination, in the manufacture of containers suitable for use in the RBC products of the present disclosure are described in U.S. Pat. Nos. 5,026,347, 4,140,162, 5,849,843, and 6,579,583, all of which are incorporated herein by reference in their entireties. Of course, it will be appreciated that even in containers where the walls 12 are made without any PVC, some PVC may be present in a small amounts in the container as a whole, as ports 16 may often include plasticized PVC.

Containers for the storage of red blood cells in accordance with the present disclosure include at least one extractable agent that is or includes a paraphthalate ester. In a preferred embodiment, the paraphthalate ester is terephthalate ester. In an even more preferred embodiment, the terephthalate ester is di-2-ethyl hexyl terephthalate (DEHT or DOHT). DEHT is available from Eastman Chemical Co. of Kingsport, Tenn. under the product name Eastman 168.

Thus, a preferred composition of the present disclosure includes polyvinyl chloride and DEHT in an amount effective to suppress hemolysis of red blood cells. In one embodiment, the composition of the present disclosure includes approximately 20-45% by weight, terephthalate ester, such as DENT. In a more specific embodiment, the composition of the present disclosure includes approximately 30% of a terephthalate ester such as DEHT. The remainder of the composition is made up of the base polymeric material such as, but not limited to, polyvinyl chloride and optionally stabilizers and lubricants. Thus, in a specific, non-limiting example, the composition includes approximately 55%-80% polyvinyl chloride and approximately 20%-45% terephthalate ester. The composition may also include stabilizers and lubricants. An example of a stabilizer is epoxidized oil. In one non-limiting example, compositions described herein may include greater than 3.0% of epoxidized oil and less than approximately 1.0% of a co-stabilizer such as metal stearate. Stabilizers other than epoxidized oil may also be used.

In another embodiment, the composition of the present disclosure may include polyvinyl chloride, one or more extractable agents or plasticizers such as terephthalate ester and be free of or essentially free of phthalate esters or orthophthalate esters. Thus, by way of example, compositions of the present disclosure include a polymeric material such as PVC and at least two extractable agents or plasticizers, one of which is a terephthalate ester and the other of which is a non-phthalate and non-orthophthalate ester plasticizer (i.e., is not DEHP). Preferably, such additional non-phthalate esters have a molecular weight of between approximately 350 to 550. More specific examples of such non-phthalate or non-orthophthalate agents that may be suitable for use in the PVC containers with a terephthalate ester include, for example, epoxidized oil, the family of citrate esters, such as n-butyryl-n-hexyl citrate (BTHC), acetyltri-n-butyl citrate (ATBC), both of which are described in U.S. Pat. No. 5,026,347, and 1,2-cyclohexanedicarboxylic acid diisononyl ester, known by its trade name, DINCH. Thus, in accordance with the present disclosure, at least two, preferably non-phthalate, extractable agents/plasticizers may be combined with the base polymeric material (e.g., PVC) in one embodiment of the composition of the present disclosure.

In a further embodiment, the plastic composition of the present disclosure may include first and second extractable agents/plasticizers (wherein one of the first or second agents/plasticizers is preferably DEHT or other terephthalate ester) and at least a further or third plasticizer. The further or third agent/plasticizer may likewise be a non-phthalate plasticizer. The third plasticizer may be a plasticizer that is not readily extractable or is marginally extractable, such as TEHTM or epoxidized oil (which also acts as a stabilizer) or a plasticizer that is more readily extractable, such as the citrate ester acetyltri-n-butyl citrate (ATBC) or DINCH, and is also effective in suppressing hemolysis. Additional agents or plasticizers may further be included in the formulation of the containers described herein.

Thus, in accordance with the examples discussed above, compositions of the present disclosure may include approximately 55%-80%, by weight, PVC resin and approximately 20%-45%, by weight, of at least one extractable agent that is or includes a terephthalate ester and one or more other plasticizers (extractable, marginally extractable or readily extractable) such as BTHC, DINCH, TEHTM, epoxidized oil, and stabilizers and lubricants. Where the composition includes terephthalate and one or more additional plasticizers, the terephthalate ester may constitute at least approximately 5% of the total plasticizer content.

The containers described herein may be used in the storage of red blood cell compositions. Such compositions may be concentrated RBCs or concentrated RBCs with an additive solution, i.e., an RBC product. The additive solutions may be any known additive solution including Adsol (AS-1) available from Fenwal, Inc. More preferably, the additive solution may be generally hypotonic and typically (but not necessarily) do not include sodium chloride. Such storage solutions also include a nutrient, a buffer and other additives such as sodium citrate. Solutions suitable for use in the storage of RBCs in accordance with the present disclosure typically have a pH of about 8.0 or higher and are described in U.S. Patent Publication Nos. US 2009/0239208 and US 2011/0117647, both of which are also incorporated herein by reference. In a specific embodiment, the additive solutions include between about 1 to 2.2 mM of adenine; about 20 mM to about 110 mM of mannitol; about 2.2 mM to about 40 mM sodium citrate; about 16 mM to about 30 mM sodium phosphate dibasic and about 20 mM to about 140 mM of glucose. The pH of the additive solution is above about 8.0.

Thus, concentrated RBCs with some or most of the plasma removed are combined with additive solutions of the type described above to provide the RBC composition. In one embodiment, the RBC composition includes between about 80 to 150 ml of the additive solution combined with about 180 to 250 nil of the concentrated RBCs. More preferably, the volume of additive solution may be about 100-110 ml. The compositions of the container wall (as described herein) that contacts the RBCs and the storage medium provide the RBCs with a storage environment that suppresses and otherwise maintains level hemolysis.

In the collection of RBCs, it is typical to remove leukocytes from, or at least reduce the number of leukocytes in, the RBCs prior to their storage and transfusion. RBCs suspended in an additive solution are often subjected to a leuko-reduction step which commonly includes filtration of the RBC/additive solution. Thus, in accordance with the methods and systems disclosed herein, RBCs are subjected to a filtration step or other treatment whereby leukocytes and/or other undesirable agents or pathogens such as prions are substantially removed (or the populations of leukocytes and/or prions are substantially reduced) from the RBCs. In one embodiment, concentrated RBCs may be combined with an additive solution of the type described above and the combined concentrated RBC/additive solution composition may be subjected to the leukocyte and/or prion removal (e.g., filtration) step.

While the containers and compositions disclosed herein have been described in connection with various embodiments, it will be apparent to those skilled in the art that modifications and variations may be made thereto without departing from the spirit and scope of the invention.

The invention claimed is:

1. A medical container for storing red blood cells comprising:
one or more container walls defining an interior chamber, said container wall(s) comprising a single sheet made of a composition comprising one or more polymeric materials and (b) only two extractable agents wherein one of said two extractable agents is di-2-ethyl hexyl terephthalate and the other of said two extractable agents is a citrate ester, wherein said two extractable agents are present in an amount effective to suppress hemolysis in red blood cells.

2. The container of claim 1 wherein said polymeric material comprises polyvinyl chloride.

3. The container of claim 1 wherein said at least two extractable agents comprise between approximately 20%-45%, by weight, of said composition.

4. The container of claim 1 wherein said di-2-ethyl hexyl terephthalate comprises approximately 30% by weight of said composition.

5. The container of claim 1 wherein said composition is free of or essentially free of phthalates and ortho-phthalates.

6. The container of claim 1 wherein said composition comprises approximately 55%-80% polyvinyl chloride, stabilizers and lubricants.

7. The container of claim 1 wherein said composition comprises approximately 55%-80% polyvinyl chloride, approximately 20%-45% di-2-ethyl hexyl terephthalate.

8. The container of claim 3 wherein at least approximately 5% of said plasticizer comprises said di-2-ethyl hexyl terephthalate.

9. The container of claim 8 wherein said container is sterilized by autoclaving.

10. The container of claim 1 further comprising one or more ports that provide(s) a flow path in flow communication with said interior chamber.

11. The container of claim 10 wherein said one or more port(s) is made of a material comprising polyvinyl chloride.

12. A red blood cell product comprising:
a container comprising one or more walls defining an interior chamber wherein the wall(s) is/are made of a monolayer of a composition comprising one or more polymeric materials and only two extractable agents wherein one of said two extractable agents is di-2-ethyl hexyl terephthalate, and the other of said two extractable agents is a citrate ester, wherein said two extractable agents are present in an amount that is effective to suppress hemolysis in red blood cells, and wherein said chamber is configured to contain a suspension of red blood cells contained within said chamber, said suspension comprising:
(a) concentrated red blood cells; and
(b) an additive solution comprising at least a nutrient and a buffer.

13. The red blood cell product of claim 12 wherein said polymeric material is polyvinyl chloride.

14. The red blood cell product of claim 12 wherein said composition comprises 20%-45%, by weight, of said di-2-ethyl hexyl terephthalate.

15. The red blood cell product of claim 12 wherein said container further comprises another plasticizer.

16. The red blood cell product of claim 12 wherein said additive solution is a hypotonic solution having a pH of at least approximately 8.0.

17. A medical container for storing red blood cells comprising: one or more container walls defining an interior chamber, wherein said container wall(s) comprises a single sheet made of a composition comprising 55%-80% by weight of one or more polymeric materials and (b) 20%-45% of extractable agents including a single terephthalate ester that is di-2-ethyl hexyl terephthalate and a non-phthalate agent wherein at least the amount of di-2-ethyl hexyl terephthalate is effective to suppress hemolysis in red blood cells.

18. The medical container of claim 17 wherein said non-phthalate agent is a plasticizer.

19. The medical container of claim 18 wherein said plasticizer is selected from the group consisting of citrate ester, DINCH, TEHTM and epoxidized oil.

20. The medical container of claim 19 wherein said citrate ester is n-butyryl-n-hexyl citrate.

21. The medical container of claim 17 wherein said non-phthalate agent is extractable.

22. The medical container of claim 19 wherein said citrate ester is acetyl tri-n-butyl citrate.

23. A medical container for storing red blood cells comprising: one or more container walls defining an interior chamber, said container wall(s) are made of a single layer of a composition comprising one or more polymeric materials and (b) at least two extractable agents wherein only one of said at least two extractable agents is a terephthalate ester, wherein said terephthalate ester is di-2-ethyl hexyl terephthalate and the other of said at least two extractable agents is a citrate ester, wherein said at least two extractable agents are present in an amount effective to suppress hemolysis in red blood cells.

* * * * *